United States Patent [19]

Vardimon

[11] Patent Number: 4,871,310

[45] Date of Patent: Oct. 3, 1989

[54] FUNCTIONAL ORTHOPEDIC MAGNETIC APPLIANCES (FOMAS)

[76] Inventor: Alexander D. Vardimon, 1337 E. Madison Park, Chicago, Ill. 60615

[21] Appl. No.: 79,133

[22] Filed: Jul. 29, 1987

[51] Int. Cl.$^4$ .............................................. A61C 7/00
[52] U.S. Cl. ......................................... 433/19; 433/18
[58] Field of Search ...................... 433/18, 19, 24, 189

[56] References Cited

U.S. PATENT DOCUMENTS

| | | | |
|---|---|---|---|
| 3,353,271 | 11/1967 | Blechman | 433/18 |
| 4,424,030 | 1/1984 | Smiley et al. | 433/18 |
| 4,671,767 | 6/1987 | Blechman | 433/18 |

*Primary Examiner*—Robert Peshock
*Attorney, Agent, or Firm*—Jerome Goldberg

[57] ABSTRACT

A functional orthopedic magetic appliance (FOMA) for correcting sagittal disproportions of the jaws in the form of skeletal malocclusions occurring when one jaw jets further outward anteriorly than the other jaw; and may also be used when the sagittal imbalance is associated with vertical jaw relationship problems to correct an accompanied open bite or deep bite. The FOMA includes at least one pair of anterior magnetic units in attractive orientation, with an upper magnetic unit secured to the upper jaw and a lower magnetic unit secured to the lower jaw. The anterior magnetic unit can be placed labial or lingual to the dental arch. The magnetic unit associated with the forward extending jaw is positioned anterior or forward of the other magnetic unit when the mouth is open and almost no attractive force is operating. When the mouth moves toward a closed condition, the magnetic units come into contact (no air gap) with each other, thereby pulling the mandibular jaw toward the maxillary jaw in the direction for reducing the skeletal imbalance. Repositioning of the lower jaw to a new sagittal position is achieved by gradual or abrupt anterior/posterior adjustments of at least one magnetic unit within the plane of skeletal imbalance to the point where the attractive magnetic force causes full overlapping of juxtaposed magnetic units and overcomes the counterforce of the stretched mandibular muscles. Also, at least one of the anterior magnetic units may be adjustable in the vertical direction. Posterior positioned upper and lower magnets may be incorporated in the FOMA having poles in an attractive and repulsive orientation for the correction of deep bite or open bite malocclusions, simultaneously with the sagittal correction of the upper or lower jaws. The FOMA can be constructed as a fixed or removable appliance, and can also be integrated with an extra oral appliance such as a headgear.

44 Claims, 4 Drawing Sheets

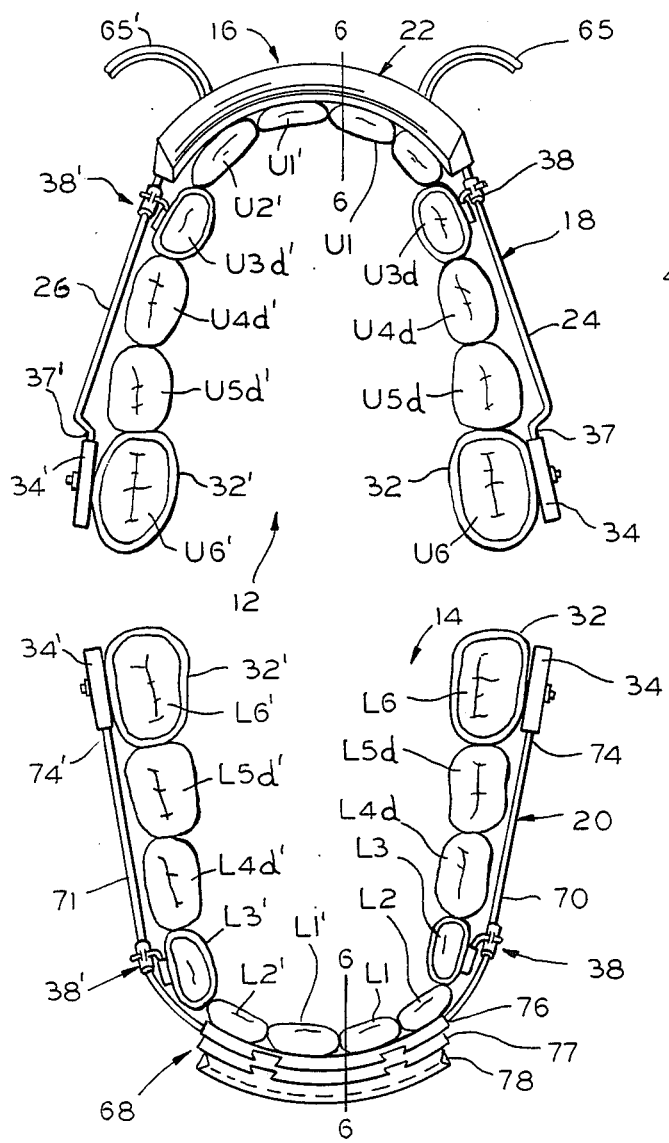
FIG.1
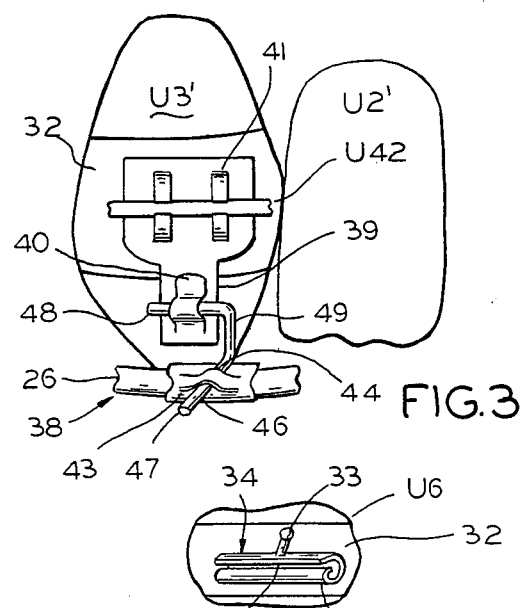
FIG.3
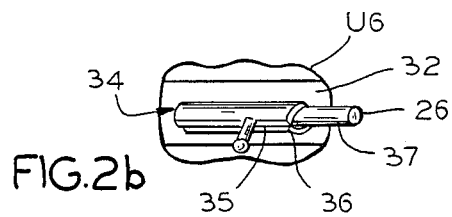
FIG.2a
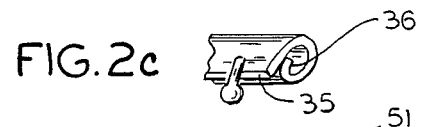
FIG.2b
FIG.2c
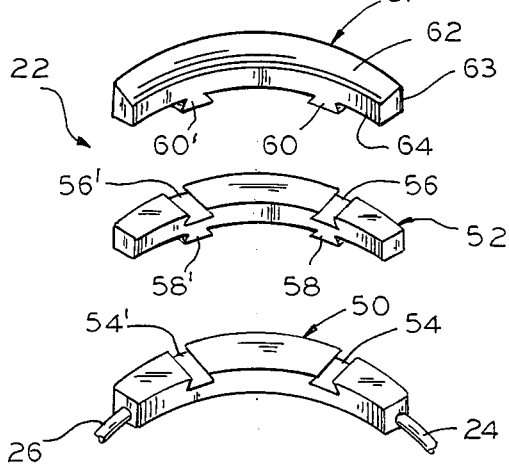
FIG.4
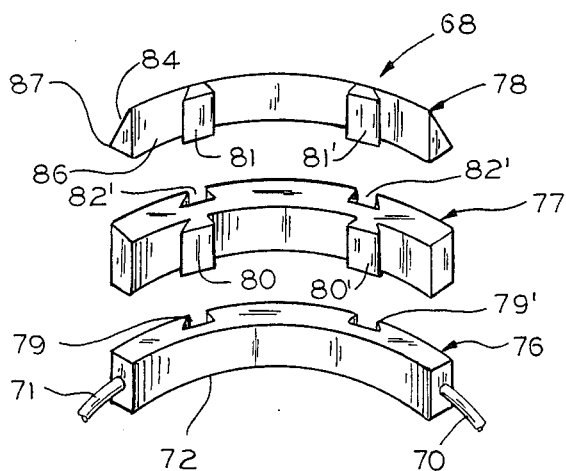
FIG.5

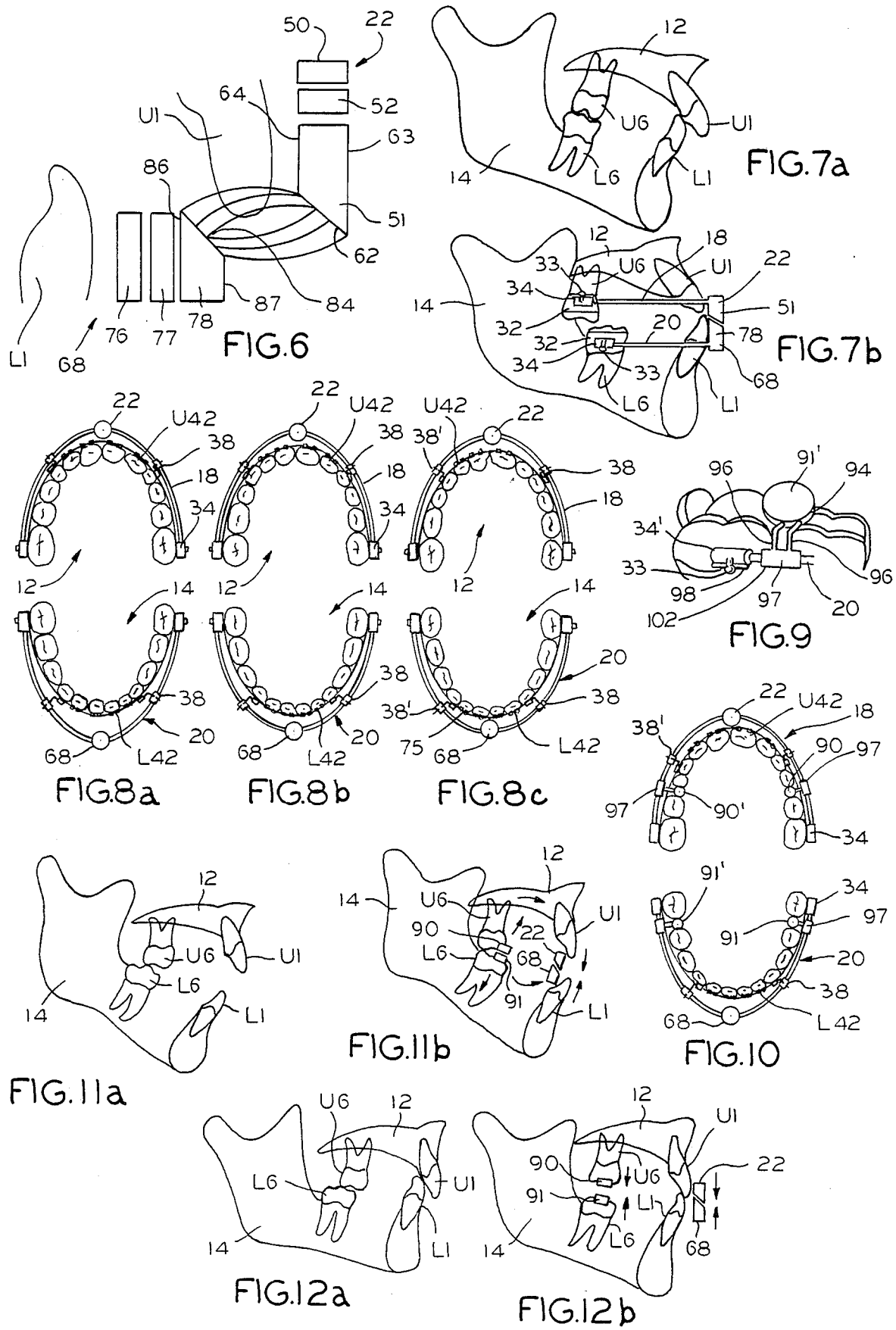

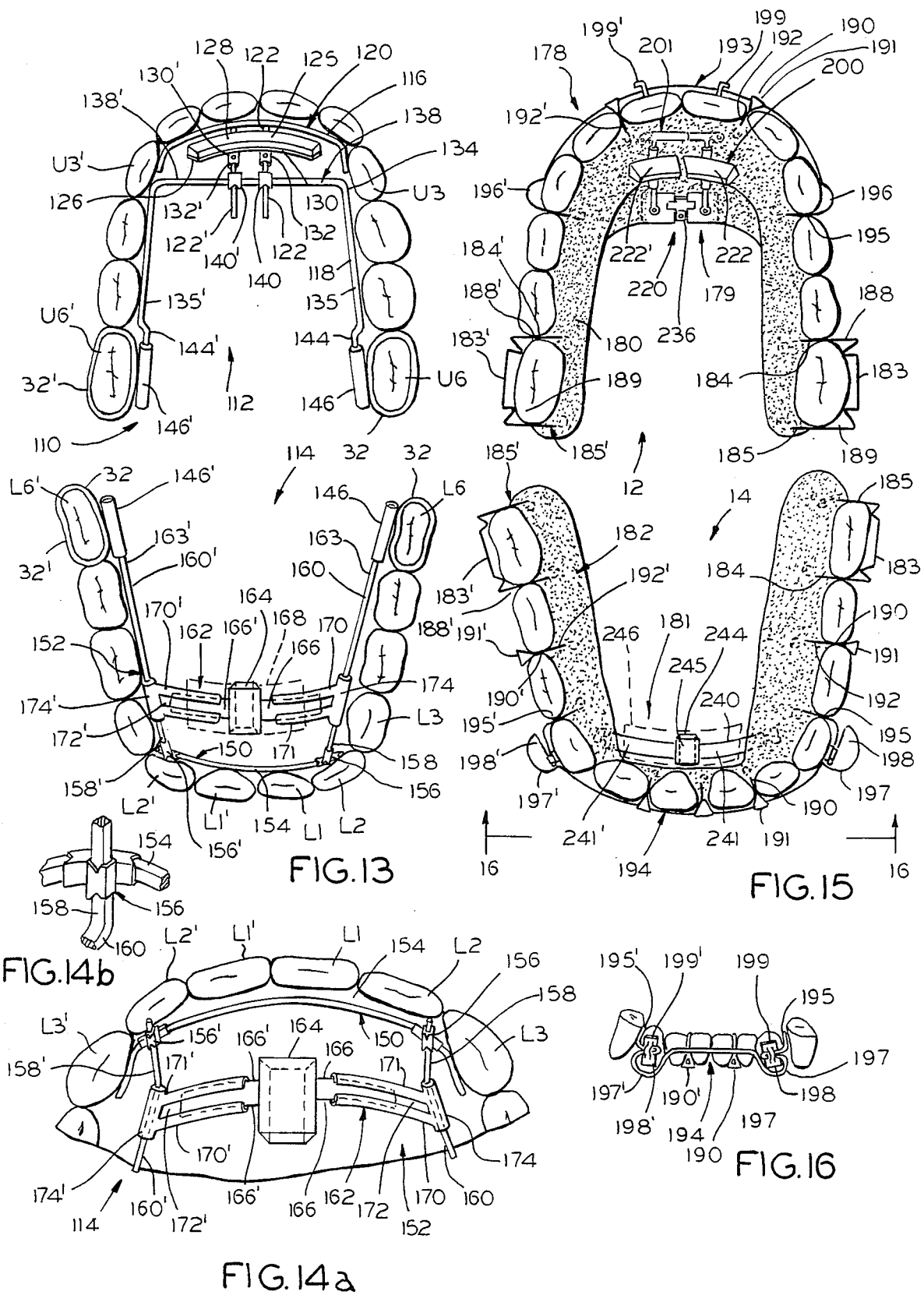

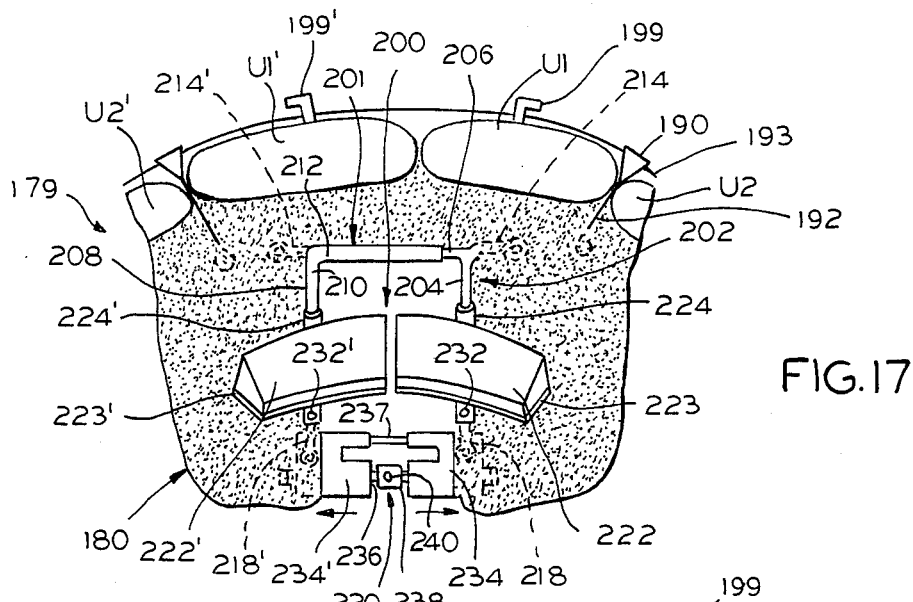
FIG.17
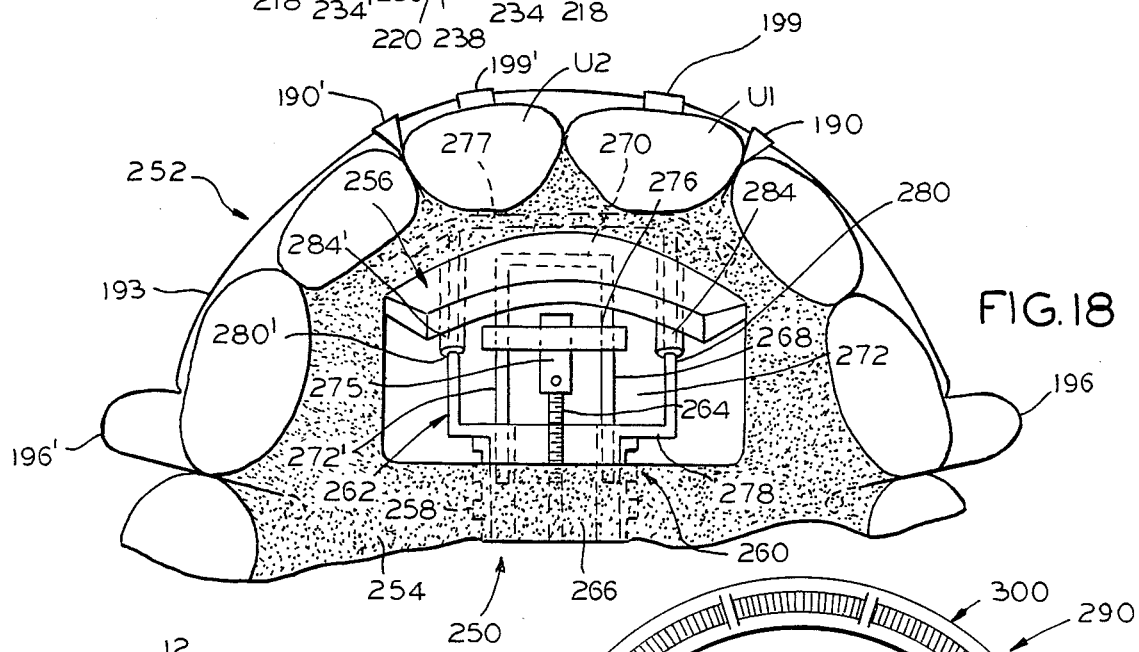
FIG.18
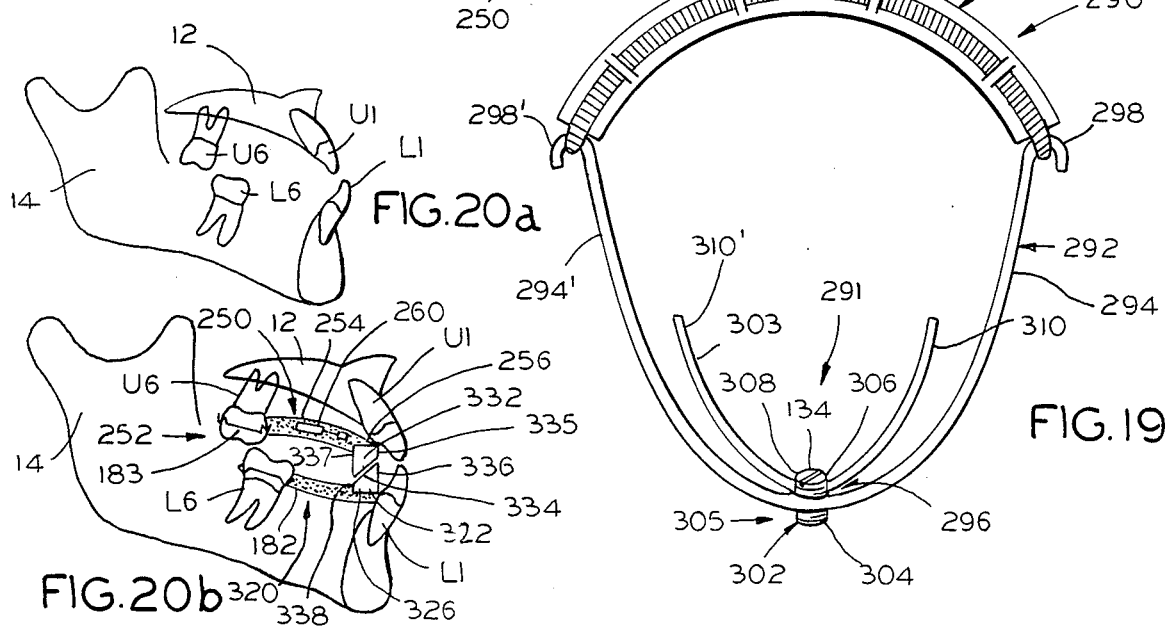
FIG.20a
FIG.20b
FIG.19

FUNCTIONAL ORTHOPEDIC MAGNETIC APPLIANCES (FOMAS)

BACKGROUND OF INVENTION

This invention of a functional orthopedic magnetic appliance (FOMA) relates generally to the field of orthodontics and more specifically to orthopedic correction of dentofacial imbalances in the form of sagittal jaw malrelationships known as skeletal Class II and Class III malocclusions; and still more specifically relates to the correction of the vertical dento-alveolar or skeletal imbalances such as an open bite or deep bite of the teeth simultaneously when correcting for the sagittal imbalances.

Skeletal Class II malocclusion occurs generally when the lower jaw is retruded (underdeveloped) in relation to the upper jaw. Skeletal Class III malocclusion occurs in general when the lower jaw jets forward (overdeveloped) in relation to the upper jaw.

Functional orthopedic appliances for the correction of sagittal interjaw discrepancies by guiding the growth potential of the jaws during the accelerated body growth period, appeared in Europe early in the 20th century. The application of permanent magnets in dentistry, in particular in orthodontics, significantly increased after two major developments in the magnetic materials: the first was in the early 1960s with the introduction of rare earth alloys in the form of samarium cobalt compounds identified as $SmCo_5$ and $Sm_2Co_{17}$; and in recent years, a stronger magnetic alloy identified as $R_2Fe_{14}B$, where R is the rare earth element usually neodymium, has been used and is preferred by the inventor for orthodontic-orthopedic corrections.

U.S. Pat. No. 4,424,030, SMILEY et al (1984), discloses a magnetic osteogenic and orthodontic appliance having one magnetic unit attached to an upper arch wire secured to the upper jaw and another magnetic unit attached to a lower arch wire secured to the lower jaw. The magnetic units are placed on the buccal side of the dental arch, and create a magnetic force which cause tooth movement. SMILEY alleges that the effect of the changing magnetic field caused by mandibular movement during mastication, speech etc. accelerates bone formation in the void created from the tooth movement. An air gap is maintained between the magnetic units inorder to achieve the desired low frequency magnetic field.

In U.S. Pat. No. 4,457,707, SMILEY et al (1984), magnetic or electromagnetic appliances attached to the jaw provide corrective movement of individual teeth including torquing of the anterior teeth.

In U.S. Pat. No. 4,511,330, SMILEY et al (1985), an extra-oral oral magnetic unit located on the cheek by being attached to a headgear strap coacts with one or more intra-oral magnets. The external magnetic unit reciprocated with the internal magnets provide a varying electromagnetic field alleged to aid in periodontic and/or orthodontic therapy by its presumably osteogenic effect.

In U.S. Pat. No. 4,396,373, DELLINGER (1983), an orthodontic magnetic appliance is disclosed having two rigid caps with each containing a magnet. One cap is secured to a tooth or teeth in the upper jaw and the other cap is secured to a tooth or teeth in the lower jaw. The magnets are in registry with each other when the mouth is closed and exert a magnetic force in a direction substantially vertical to the occlusal plane, for intruding or extruding teeth. The appliance is removable when used for intruding teeth, and is fixed when used for extruding teeth.

In my German Pat. No. DE2857 736 C2, VARDIMON (1982), upper and lower magnets are positioned offset in the sagittal plane with the poles orientated in an attractive arrangement. The magnetic force is sufficient to hold the lower jaw in a sagittal captured posture and to maintain the mouth closed, thereby counteracting the normal stretching force of the mouth opening muscles, the effects of which are to reinforce the treatment process. The magnets are usually incorporated in double thrusting plates (Vorschubdoppel platten).

In my German Pat. No. DE 2840 370 C3, VARDIMON (1982), magnets placed in an attractive arrangement are utilized to pull a forward projecting tooth backward or in the posterior direction; and conversely, magnets placed in a repelling configuration push a backward extending tooth in the forward or anterior direction.

SUMMARY OF THE INVENTION

The functional orthopedic magnetic appliance of this invention corrects skeletal malocclusion such as occurring when one jaw jets further outward anteriorly than the other jaw, by repositioning the lower or mandibular jaw with respect to the upper or maxillary jaw within the sagittal plane in a direction to reduce the skeletal imbalance. The magnetic appliance comprises an anterior upper magnetic unit secured to the upper jaw and a juxtaposed anterior lower magnetic unit secured to the lower jaw, in a magnetically attractive orientation. The magnetic unit associated with the anterior jaw is positioned anterior to the counterpart magnetic unit associated with the posterior jaw (when no magnetic force is being exerted). The magnetic attractive force exceeds the counterforce of the stretching mandibular muscles normally tending to open the mouth and restore the lower jaw to its original malformed position. When the mouth moves from an open toward a closed condition the juxtaposed magnetic units come into contact with each other in a full overlapping of adjacent pole surface areas, thereby shifting the lower jaw to its new acquired sagittal position. At least one of the magnetic units is adjustable in the anterior/posterior direction, and at least one of the magnetic units is adjustable in the vertical direction.

Guiding the skeletal growth of the jaws is achieved by changing the antero-posterior posture of the lower jaw with respect to the upper jaw. The corrective treatment described herein should be given during the period of accelerated statured growth, so that the bone may be reconstructed to cure the sagittal discrepancy. An anterior repositioning of the lower jaw is performed in the correction of a skeletal Class II malocclusion; and, conversely, a posterior repositioning of the lower jaw is performed in the correction of a skeletal Class III malocclusion. The degree or amount of adjustment of the anterior pair of magnets or any additional posterior juxtaposed magnets alter the extent of repositioning of the lower jaw and is, therefore, a function of treatment goals.

In the correction of skeletal Class II malocclusions either gradual (step by step) or abruptive (one or two steps) adjustments of the sagittal distance between the upper and lower magnets are made during treatment, depending upon the individual response and severity of the case. A mild skeletal Class II malocclusion can be treated by positioning the upper magnet further anteriorly than the counterpart lower magnet, at a sagittal distance approximately equal or exceeding the sagittal distance of the interjaw discrepancy. When the mouth moves toward a closed condition, the upper and lower magnets contact each other with sufficient force to overcome the counterforce from the muscles of the lower jaw.

Severe skeletal Class II malocclusions require several adjustments of the sagittal distance between the juxtaposed upper and lower anterior magnets to achieve successive permanent and partial anterior repositioning of the lower jaw. (A partial repositioning of the lower jaw is any reposition which is less than a total repositioning for deriving a correct interjaw relationship.) At the beginning of treatment when the mouth is in an open position the upper and lower magnets are sagittally spaced apart to provide only the first partial correction. When the mouth moves to a closed condition the magnetic force is sufficient to overcome the counteracting force of the lower jaw muscles, and the magnetic surfaces overlap and contact each other. Thus, only partial anterior repositioning of the lower jaw occurs with each activation of the magnets. When there is a cessation of the muscle tension due to the guided bone growth in the direction for reducing the sagital discrepancy and the adaptation of the muscle and bone to the captured position of the lower jaw, the patient is ready to advance to the next treatment step. The sagittal distance between the upper and lower magnets is then increased, by moving the lower magnet in the posterior direction (or the upper magnet in the anterior direction) to reactivate the treatment. The step by step activation process is complete when the lower jaw has permanently advanced in the anterior direction to the desired position fully correcting the malocclusion.

Skeletal Class III malocclusion is corrected only by the gradual successive adjustment of the juxtaposed upper and lower magnets. Thus, each activation of the magnets when the mouth moves toward a closed position causes only partial posterior repositioning of the lower jaw. The posterior sagittal distance between the juxtaposed anterior magnets is incrementally increased when the muscle and bone adapt to the newly acquired posterior posture of the lower jaw (when this occurs the muscle tension which tends to dislodge the lower jaw from its captive position has virtually ceased) and the desired bony remodelling (growth restriction for a Class III interjaw discrepancy) has been accomplished.

BRIEF DESCRIPTION OF THE DRAWINGS

Referring to the drawings in which the same characters of references are employed to indicate corresponding similar parts throughout the several figures of the drawings:

FIG. 1 shows a bottom view of the upper part of the labial located fixed functional orthopedic magnetic appliance (FOMA) (also including an extraoral appliance) secured to the upper jaw and a top view of the lower part of the appliance attached to the lower jaw, viewed on the occlusal plane between the upper and lower jaws, and embodying the principles of the invention.

FIG. 2a illustrated a perspective side view of a shunted tube in an unlocked position attached to the molar band.

FIG. 2b illustrates a similar view as FIG. 2a but showing the shunted tube in a closed position securing a posterior end of the magnetic bow.

FIG. 2c is a fragmentary view similar to FIG. 2b but without the posterior end of the magnetic bow.

FIG. 3 shows a side view of the attachment between the FOMA in FIG. 1 and a canine tooth.

FIG. 4 is a perspective view (bottom to top) of the component parts of the upper magnetic unit of FIG. 1.

FIG. 5 is a perspective view (posterior to anterior) of the component parts of the lower magnetic unit of FIG. 1.

FIG. 6 is a fragmentary schematic view of the upper and lower magnetic units taken on the sagittal plane of the line 6—6 in FIG. 1 to show the reciprocating magnetic force lines acting between the upper and lower jaws.

FIG. 7a is a side view illustrating the relationship between the upper and lower central incisors and first molars in a skeletal Class II malocclusion with the upper jaw jetting outward with respect to the lower jaw.

FIG. 7b is also a side view illustrating the relationship between the upper and lower central incisors and first molars after a labial located fixed FOMA II caused a forward displacement of the lower jaw.

FIG. 8a is a view taken on an occlusal plane between the upper and lower jaws to show the position of the upper and lower magnetic bows of a labial located fixed FOMA II at the beginning of the orthopedic treatment, for a skeletal Class II malocclusion.

FIG. 8b is a view similar to FIG. 8a to show the position of the upper and lower magnetic bows of a labial located fixed FOMA II during the orthopedic treatment.

FIG. 8c is a view similar to FIG. 8a to show the position of the upper and lower magnetic bows of a labial fixed FOMA II at the end of the orthopedic treatment.

FIG. 9 is a fragmentary perspective view of a posterior magnet positioned on top of posterior teeth.

FIG. 10 is a view similar to FIG. 8a of a FOMA also including posterior magnets.

FIG. 11a is a side view of the upper and lower jaws in a skeletal Cl. II malocclusion associated with an open bite configuration.

FIG. 11b is a side view showing the relationship of juxtaposed anterior attractive magnets and posterior repulsive magnets to correct the malocclusion depicted in FIG. 11A.

FIG. 12a illustrates a fragmentary side view of a skeletal Class II malocclusion accompanied with a deep bite.

FIG. 12b illustrates the relationship of juxtaposed anterior and posterior attractive magnets for correcting sagittal imbalance and the deep bite malocclusion of FIG. 12a.

FIG. 13 illustrates a bottom view of the upper part and a top view of the lower part of a lingually located fixed functional orthopedic magnetic appliance (FOMA II) secured respectively to the upper jaw and lower jaw, viewed on the occlusal plane between the upper and lower jaws, and embodying the principals of the invention.

FIG. 14a illustrates an enlarged view of the lower anterior part of the lingual magnetic appliance of FIG. 13.

FIG. 14b is an enlarged view of the double crimpable connector linking the anterior linqual arch wire with a vertical bar.

FIG. 15 shows a bottom view of the upper part and a top view of the lower part of a lingually located removable functional orthopedic magnetic appliance secured respectively to the upper and lower jaws incorporating a transversal expansion mechanism, and embodying the principles of the invention.

FIG. 16 is a front view, taken on the plane of the line 16—16 in FIG. 15, viewed in the direction indicated, to illustrate the lower labial bow of the appliance in FIG. 15.

FIG. 17 is an enlarged view of the upper magnetic arrangement of FIG. 15 and the associated transversal and postero-anterior adjusting unit.

FIG. 18 illustrates a bottom view of the upper part of a removable lingual FOMA III appliance secured to the upper jaw, and embodying the principles of the invention.

FIG. 19 illustrates a head gear arrangement forming part of an upper fixed functional orthopedic magnetic appliance and including a vertically adjustable magnetic means.

FIG. 20a illustrates a side view of a skeletal CL. III malocclusion; and

FIG. 20b is a schematic side view of a removable FOMA III appliance showing the inclination of the upper and lower magnetic units.

DESCRIPTION OF THE PREFERRED EMBODIMENTS

The functional orthopedic magnetic appliances ("FOMAs") disclosed herein each includes at least one pair of anterior magnets in an attractive force configuration with an upper magnet secured to the maxilla or upper jaw 12 and a lower magnet secured to the mandible or lower jaw 14. If the lower jaw 14 is retruded with respect to the upper jaw 12 than the upper magnet is always placed anterior with respect to the lower magnet during treatment, and these functional orthopedic appliances are referred to as FOMAs II. Conversely, if the lower jaw 14 jets outward further than the upper jaw 12, the upper magnet is always placed posterior with respect to the lower magnet during treatment, and these orthopedic appliances are referred to herein as FOMAs III.

The construction of the FOMAs disclosed herein is based upon the following principals:

1. Orthopedic (skeletal) and not orthodontic (dental) movements, although orthodontic corrections may be carried on simultaneously but independently from the orthopedic corrections described herein;

2. Sagittal displacement with choice of readjustment (incremental or abruptive) of juxtaposed pairs of magnets according to the severity of the skeletal malocclusion and the jaws' response to guided growth;

3. Vertical displacements of the magnets to maintain a no air gap contact between juxtaposed pair of magnets in an attractive orientation;

4. Choice of integrating an extra oral appliance such as an upper headgear with the FOMAs;

5. Incorporating additional magnets for the correction of dentoalveolar or skeletal vertical problems; and 6. Feasibility to perform as a fixed or removable appliance.

The orthopedic correction of the jaw is advised to be instituted during the child's growth period, which extends shortly prior to, during and shortly after the transition from the deciduous to the permanent dentition (mixed dentition). Therefore, the figures will show a total of 24 teeth instead of 32 and each quadrant will include six teeth: central incisor 1, lateral incisor 2, lower canine (cuspid) 3 and upper deciduous canine 3d, deciduous molar 4d, deciduous molar 5d and permanent molar 6. A prefix "U" is used when referring to teeth of the upper jaw 12, and a prefix "L" is used when referring to teeth of the lower jaw 14. A suffix "'" prime is used to identify teeth and various other components in the right quadrant of each jaw 12,14.

Referring now more specifically to FIG. 1 of the drawings, a functional orthopedic magnetic appliance configuration is illustrated and identified generally by the reference numeral 16, which is a fixed labial FOMA II. The fixed labial appliance 16 includes an upper magnetic bow 18 secured to the upper jaw 12 and a lower magnetic bow 20 secured to the lower jaw 14.

The upper magnetic bow 18 includes an anterior upper magnetic unit 22 in an arcuate shape centrally positioned between opposed side portions 24, 24'.

Stainless steel bands 32,32' (FIGS. 2a and 2b) are positioned around the molars U6,U6' and canines U3d, U3d' respectively. A shunted tube 34 is soldered or otherwise permanently attached to each molar band 32,32'. The shunted tube 34 is split and includes overlapping lips 35,36. When the lips are apart (FIG. 2a), the corresponding posterior end 37 or 37' of the magnetic bow 18 is inserted unrestrained into the tube. Once the sagittal position of the magnetic bow is determined, the shunt or handle 33 is pulled downward (FIG. 2b) and the corresponding posterior end 37 or 37' of the magnetic bow 18 is locked by the tight grip of the tube's lips 35,36 (which functions to reduce the tube's inside diameter-FIG. 2c. The inner surface of the shunted tube 34 and the corresponding clamped surface of the posterior ends 37,37' of the magnetic bow 18 have rough surface areas to increase friction.

Canine anchorage means indicated generally by the reference numeral 38 (FIG. 3) are used for securing the side portions 24,24' of the upper bow 18 to the canines U3d and U3d'. The anchorage means 38 comprises a cleat base 39 attached to band 32 or 32' or directly bonded to the buccal crown surface of the corresponding upper deciduous canines U3d or U3d', and a cleat 40 is permanently attached to the cleat base 39. The cleat base 39 may also be part of an edgewise bracket 41 attached to the band 32 or 32' or directly bonded to the corresponding canine for holding an upper arch wire U42. A slidable crimpable sleeve 43 encircles and is positioned on the corresponding side portions 24 or 24' and secured thereto adjacent the cleat 40. The sleeve 43 includes a clasp 44.

An angled hook 46 links side portion 24 or 26 of the magnetic bow 18 to the corresponding canine. One end 47 of hook 46 is permanently crimped in the clasp 44 and the opposite end 48 press fits into the cleat 40 (each time the FOMA is inserted in the patient's mouth). The sleeve 43 is also permanently crimped for a tight association with the magnetic bow 18. The hook 46 is bent so that both ends 47,48 are substantially perpendicular to the intermediate portion 49, therebetween, and the ends 47,48 are perpendicular to each other (not connected to each other).

Turning now to FIG. 4, it will be seen that the upper anterior magnetic unit 22 comprises a supporting base 50, an upper magnetic member 51, and an intermediate connector member 52 positioned between the suporting base 50 and the magnetic member 51. The use of one or more intermediate connector members 52 enable the vertical height of the upper anterior magnetic unit 22 to be adjusted.

The supporting base 50 includes a pair of grooves 54,54' on its inferior (bottom) side. Grooves 56,56' are formed on the inferior side of the connector 52 and a pair of tongues 58,58' protrude outward from the opposite or superior (top) side of the connector 52. Tongues 60,60' protrude outward from the superior side 61 of the upper magnetic member 51. The tongues and grooves enable a dovetail or interlocking connection between parts. The supporting base 50 may either receive the tongues 58,58' from the connector 52 or tongues 60,60' from the magnetic member 51. Thus, if the connector member 52 is used, tongues 58, 58' of the connector 52 fit into the supporting base 50 and tongues 60,60' of the magnetic member 51 fit into the grooves 56,56' in the connector 52.

The supporting base 50 would generally be constructed from a non-magnetic material such as stainless steel or a suitable plastic. The connector member 52 may be constructed from a magnetic material if an increase in the magnetic field is desired, or from a non-magnetic material such as teflon or acrylic. Thus, the connector 52 may provide adjustment of the magnetic field strength and an extension or adjustment of the vertical distance between the upper or lower magnetic bows 18,20.

The upper magnetic member 51 has an arcuate shape and has in the case of FOMA II an inferior surface 62 sloping inward from a maximum height at the front side 63 to a minimum height at the back side 64 (see FIG. 6).

The upper magnetic bow 18 may include a pair of branches 65,65' protruding from the supporting base 50 to provide a head gear arrangement. The branches 65,65' extend outside the mouth along the cheeks to receive a head gear strap. The head gear arrangement in the upper magnetic bow 18 provides an additional force source to drive the upper molars and/or the upper dental arch and/or the whole maxilla in the posterior direction and/or to prevent further anterior movement of the mid face. Thus, orthodontic/orthopedic correction of the upper jaw 12 may take place simultaneously with the orthopedic correction of the lower jaw 14 (see also FIG. 19).

The lower magnetic bow 20 (FIG. 1) is similarly constructed as the upper magnetic bow 18 and comprises an arcuate lower magnetic unit 68 centrally positioned between side portions 70,71. To secure the lower magnetic bow 20 inside the lower jaw 14, the posterior ends 74,74' of the magnetic bow 20 are secured inside the shunt tubes 34,34' attached to the bands 32,32' around the molars L6,L6'.

The canine anchorage means 38,38' are used for securing the lower magnetic bow 20 to the lower canines L3,L3'. The cleat base 39 may also be part of an edgewise bracket 41 (FIG. 3) bonded to the corresponding canine or cemented via the band 32 or 32' for holding a lower arch wire L42.

Referring now to FIG. 5, the lower anterior magnetic unit 68 is shown and comprises a supporting base 76, an intermediate connector 77 and a magnetic member 78.

The supporting base 76 includes grooves 79,79' to receive the tongues 80,80' of the connector member 77 or the tongues 81,81' of the lower magnetic member 78. If the connector 77 is used, the grooves 82,82' of the connector 77 receive the tongues 81,81' of the lower magnetic member 78, and if connector 77 is not used the tongues 81,81' are received by the grooves 79,79' in the base 76.

The utilization of connector 77 or more than one of such connector 77 (for a Class II malocclusion) enables the sagittal (horizontal) distance to be reduced between the upper magnetic bow 18 and the lower magnetic bow 20 when the upper and lower magnetic members 51, 78 are sagittally spaced apart; and to increase the sagittal distance between the lower dental arch and the lower magnetic member 78, so that during corrective treatment the sagittal distance between the lower arch and the lower magnetic member 78 may be reduced by the removal of the connector(s) 77. Another means for sagittal adjustment is provided by the shunted tubes 34. The sagittal position of the lower magnetic member 78 may be adjusted corresponding to the depth that the posterior ends 74,74' extend into the tubes 34,34'. Thus, in mild or non-severe cases the fixed labial located FOMA II magnetic appliance 16 can be simplified by applying only one of the described sagittal adjustment mechanisms.

The lower magnetic member 78 also has an arcuate shape (FIG. 5) and the outer or superior (occlusal) surface 84 slopes downward from a maximum height at the rear side 86 to a minimum height at the front side 87 (FIG. 6). The complementary sloping of the occlusal surfaces 62,84 of the upper and lower magnetic members 51,78 respectively assist in obtaining the desired overlapping of opposed surface areas which directly effect the accurate performance of the FOMAs.

Turning now to FIGS. 7 and 8, the utilization of the fixed, labial functional orthopedic magnetic appliance (FOMA) II 16 for correcting the retruded (underdeveloped) lower jaw 14 with respect to the upper jaw 12 will be described.

In FIG. 7a the upper central incisor U1 and its basal bone overjets the lower central incisor L1 and its basal bone, which is illustrative of a skeletal Class II malocclusion. The action of the attractive magnetic force of the upper and lower anterior magnetic units 22,68 causes the lower jaw (mandible) 14 to thrust forward as shown in FIG. 7b, to stretch the mandibular muscles and initiating the selective guided growth of the jaws i.e. accelerating the growth of the lower jaw 14 and restricting the growth of the upper jaw 12. Finally after the completion of the treatment, there is the desired normocclusion of the skeletal and dentoalveolar components.

At the outset or initial phase of the corrective treatment (FIG. 8a), the upper anterior magnetic unit 22 shown having a disc shape, is placed anterior of the upper dental arch wire U42; and the lower anterior magnetic unit 68 is placed anterior of the lower dental arch wire L42 but is sagittally spaced posterior from the upper anterior magnetic unit 22, when the mouth is open and almost no attractive force from the magnetic units 22,68 is operating.

When the mouth moves toward a closed condition, the attractive force from the anterior magnetic units 22,68 pulls the mandible 14 toward the upper jaw 12 which is in the direction for reducing the malocclusion until the anterior magnetic units 22,68 overlap and come into contact with each other.

The magnetic contacting force is sufficient to overcome the counterforce of the stretched mandibular muscles but not of such magnitude to restrict normal functional movement of the lower jaw 14 such as deglutition, eating, speaking etc. In time the lower jaw 14 partially repositions to a new position which partially reduces the malocclusion between the upper and lower jaws 12,14, and has the effect of reducing the counterforce from the stretched mandibular muscles. Also, the sagittal distance between the upper and lower anterior magnetic units 22,68 is decreased when the mouth is open To continue the repositioning process for the lower jaw, the lower anterior magnetic unit 68 is readjusted (2nd adjustment) to increase the sagittal distance between the lower magnetic member 78 and the upper magnetic member 51 and decrease the sagittal distance from the lower dental arch (FIG. 8b). Now when the mouth moves toward a closed condition, the attractive magnetic force acts against substantially the same stretching force of the mandibular muscles as was previously present (1st adjustment). In time the lower jaw 14 again partially repositions to further reduce the malocclusion; and the sagittal distance between the upper and lower magnetic members 51,78 may again be increased (3rd adjustment) and simultaneously the sagittal distance between the lower anterior magnetic unit 68 and the lower dental arch is decreased (FIG. 8c).

The adjustments of the sagittal distances for correcting the malocclusion may be made abruptive over a few time intervals; or, depending upon the severity of the skeletal malocclusion and skeletal responses to treatment (growth guidance), may be made incrementally or gradually over numerous successive time intervals.

At the end of treatment (FIG. 8c) the lower jaw has fully repositioned to a point of normal occlusion. In the corrected position the upper and lower anterior magnetic units 22,68 would be in substantial alignment or further repositioned to establish overcorrection i.e. counteracting a relapse response.

Referring now to FIGS. 9 through 12b, the combined sagittal and vertical skeletal correction will be described. Upper posterior magnetic discs 90,90' magnetically cooperate respectively with lower posterior magnetic discs 91,91' (FIG. 10) to provide the desired vertical dentoalveolar skeletal modifications. It should be understood that although the magnets 90,90',91,91' are shown having a disc shape any other suitable shape may be used. Each posterior magnetic disc 90,90',91, & 91' is secured in an annular case 94 (FIG. 9) having a pair of fingers 96 integrally formed to a tubular sleeve 97. The upper positioned sleeves 97 are attached to the upper arch wire U42 or alternatively attached to the upper magnetic bow 18 and are movable therealong and securely crimped in place at a selected location. Similarly, the lower positioned sleeves 97 are attached to the lower arch wire L42 or alternatively attached to the lower magnetic bow 20 and are movable therealong and securely crimped in place at a selected location.

During treatment, the sagittal distance between the left upper and lower posterior magnetic discs 90,91 and the sagittal distance between the right upper and lower posterior magnetic discs 90', 91' are adjusted substantially to the same extent as required for adjusting the sagittal distance between the upper and lower anterior magnetic units 22,68.

The upper and lower adjacent posterior magnetic discs 90 with 91 and 90' with 91' overlap when the the lower anterior magnetic unit 68 moves into contact with the upper anterior magnetic unit 22. When the anterior magnetic units 22,68 are not in contact and sagittally spaced apart: the upper and lower juxtaposed posterior magnetic discs 90 with 91 and 90' with 91' do not overlap and are sagittally spaced apart substantially the same distance.

In FIG. 11a, an open bite Class II malocclusion is shown whereby the upper jaw 12 jets forward of the lower jaw 14; and only upper and lower posterior teeth occlude in maximal mouth closure. In FIG. 11b, the sagittal skeletal malocclusion is corrected by the anterior repositioning of the lower jaw and simultaneously the vertical problem is managed by intrusion of posterior dental segments.

The bilateral upper posterior magnetic discs 90,90' repel the lower magnetic discs 91,91' respectively (shown by arrows in FIG. 11b). The anterior upper and lower magnetic units 22,68 are attracted to each other and come into contact when the attractive magnetic force exceeds the counteracting force exerted by the stretching mandibular muscles. The attractive force from the anterior magnetic units 22,68 and the repulsive forces from the juxtaposed posterior magnetic discs 90 with 91 and 90' with 91' achieve a counterclockwise rotation of the lower jaw 14 (see arrows) and clockwise rotation of the upper jaw 12 (see arrows), which counteracts the undesirable growth pattern of the open bite skeletal Class II malocclusion. Since the repulsive forces from the posterior upper and lower magnetic discs 90 with 91 and 90' with 91' are weaker than the attractive forces from the anterior upper and lower magnetic units 22,68, a vertical correction of the teeth is achieved concomitant with the primary goal of the mandibular advancement.

The anterior attractive magnetic units 22,68 operating in contact and without an air gap, control the correction of the open bite imbalance by utilizing the posterior repulsive magnetic discs 90 with 91 and 90' with 91' to cause the intrusion of the posterior dentoalveolar segments and not via extrusion of the anterior dental segments. Also, the predominant anterior magnetic attractive force prevent the sideward shift of the repulsive posterior magnets, which could occur if the repulsive magnets were operating with no guidance.

Turning now to FIG. 12a, a skeletal Class II malocclusion with a deep bite is shown having a retruded lower jaw 14 with respect to the upper jaw 12 and the lower central incisor L1 occludes with the upper central incisor U1 close to the cemento-enamel junction of the latter.

In FIG. 12b, the skeletal Class II malocclusion is corrected by anterior repositioning of the lower jaw 14 toward the upper jaw 12 to achieve normal skeletal and dental occlusion. The deep bite is corrected by the simultaneous vertical spacing created between adjacent posterior teeth of the upper and lower jaws. The occlusion is maintained apart by the premature contact with no air gap between anterior magnetic units 22,68, whereas the bi-lateral juxtaposed posterior magnetic discs 90,91 (also posterior magnetic discs 90',91') attract to each other with a given air gap. The created air gap between the posterior magnetic discs induces essentially extrusion of the posterior dental segments (shown in FIG. 12b as the extrusion of the upper and lower molars U6,L6). Upper anterior magnetic unit 22 and the upper posterior magnetic discs 90,90' are displaced in the sagittal plane anterior to their lower magnetic counterparts 68,91,91' to the same extent, respectively (when no magnetic force is exerted). The posterior attractive magnetic discs 90 with 91 and 90' with 91' reinforce the anterior repositioning effect of the anterior magnetic units 22,68.

Turning now to FIG. 13, a lingual version of a fixed FOMA II is illustrated and identified by the reference numeral 110. The lingual appliance 110 includes an upper part 112 and a lower part 114. The upper part 112 comprises an anterior lingual section 116 and a posterior lingual section 118.

The anterior lingual section 116 includes a lingual upper anterior arch wire 120 extending from cuspid U3 to cuspid U3' (or U2 to U2') and two sagittal bars 122,122', spaced apart and parallel to each other. The two sagittal bars 122,122' are soldered or otherwise secured at their anterior ends to the anterior lingual arch wire 120.

An upper anterior lingual magnetic means 125 comprises a support 126 having an arcuate upper magnet 128 secured thereon. The magnet 128 is adjusted in the horizontal direction on the support 126. The support 126 includes a pair of hollow ring members 130,130' for receiving the sagittal bars 122,122'. Screws, 132 132' are threadedly associated with the ring members 130,130' respectively and extend into contact with the sagittal bars 122,122', for locking the upper magnet 128 at the desired sagittal location. Thus, the upper magnet 128 is adjusted in the postero-anterior direction (over treatment time) along the sagittal bars 122,122' by initially loosening the screws 132,132' then making the desired forward position adjustment by sliding the support 126 along the bars 122,122', and then tightening the screws 132,132'.

The upper lingual posterior section 118 of the fixed lingual FOMA II appliance 110 includes a substantially "U" shaped posterior lingual arch wire 134 formed into shape from a single straight wire, and having two side rod portions 135,135' and a transversal rod portion 138. A pair of tubes 140,140' are spaced apart and soldered to the transversal rod 138 at a central location. The space between the tubes 140,140' equals in magnitude to the distance between the bars 122,122'.

The tubes 140,140' receive the sagittal bars 122,122' and are securely crimped thereto. The upper magnet 128 is sagittally adjustible along the bars 122,122' between the anterior lingual arch wire 120 and the tubes 140,140'.

The posterior ends 144,144' of the rods 135,135' are each secured in crimpable lingual tubular members 146,146' which are soldered to bands 32,32' encircling upper molars U6, U6'. Alternatively, the shunt tube 34,34' shown in FIGS. 2a, 2b may be used in place of the lingual tubular members 146,146'

The lower part 114 of the lingual fixed FOMA II appliance 110 comprises a lower lingual anterior section 150 and a lower lingual posterior section 152. The lower lingual anterior section 150 includes a lingual lower anterior arch wire 154 also extending from cuspid L3 to cuspid L3' (or L2 to L2') and linked via double sided crimpable connectors 156,156' to a pair of vertically extending bars 158,158' of the posterior lingual section 152. The double sided crimpable connectors 156,156' connect the bars 158,158' of the lower lingual posterior section 152 respectively to the lingual anterior section 150 (FIG. 14a,b).

The lower lingual posterior section 152 includes left and right lateral or side arms 160,160' connected together by an intermediate transversal portion 162. The posterior ends 163,163' of the lateral arms 160,160' are crimped or locked in the lingual tubular members 146,146' attached to the bands 32,32' secured around the lower molars L6 and L6' respectively. Alternatively, a shunt tube 34,34' shown in FIGS. 2a, 2b may be used in place of the lingual tubular members 146,146'.

The intermediate transversal portion 162 includes a centrally positioned dove tail support table 164 having left and right wings 166,166' extending sideward mediolaterally from the midsagittal line. A lower anterior magnet 168 shown in phantom in FIG. 13 is securely fitted in the support table 164. The wings 166,166' pass through posterior track strips 170,170' and anterior track strips 171,171' having common strip bases 172,172'. The wings 166,166' are movable within the corresponding left posterior and anterior track strips 170,171 and the right posterior and anterior track strips 170',171' respectively. The left posterior and anterior tracks 170,171 and the right posterior and anterior tracks 170', 171' are attached to the left and right lateral arms 160, 160' via left and right crimpable tubes 174,174' respectively. The crimpable tubes 174,174' allow an antero-posterior adjustment of the lower anterior lingual magnet 168. The lower magnet 168 can be adjusted vertically on its support table 164 by introducing intermediate connector(s) (not presented here) similar to as shown in FIG. 4.

The fixed lingual FOMA II Appliance 110 is custom made and modified in the upper and lower plaster models of the patient's dental impression and then transferred to the mouth. The upper posterior lingual arch wire 134 is initially a straight wire. The posterior lingual arch wire 134 is then bent into the "U" configuration in accordance with the patient's upper dental cast, so that the soldered crimpable tubes 140,140' supported on the intermediate transversal portion 138 extend laterally symmetrically from the mid-sagittal line. Subsequently, the upper lingual anterior section 116 is adjusted to the model of the anterior dental arch. The upper lingual anterior section 116 and the upper lingual posterior section 118 are temporarily joined together, and placed in the mouth. The posterior ends 144,144' are inserted into the molar tubular members 146,146'. The anterior section 116 is bonded to the lingual surface of the upper incisor teeth, which, if necessary, were previously orthodontically aligned. The anterior section 116 is then tightly secured to the posterior section 118 via the crimpable tubes 140,140' and the upper magnet 128 is then adjusted horizontally with respect to the interjaw relationship.

Similar to the upper part 112, the lower part 114 of the fixed lingual FOMA II appliance 110 is adjusted on the patient's lower plaster model prior to setting in the mouth. When making the transversal adjustment on the cast model, the support table 164 is positioned substantially centered on the mid-line. The left wing 166 is passed through the left posterior and anterior tracks 170, 171 and the right wing 166' is passed through the right posterior and anterior tracks 170',171' for expanding the transverse frame to the desired span. Next the side arms 160,160' are adjusted in the antero-posterior direction and any excess length is removed prior to inserting into the molar tubular members 146,146'. Finally, the double sided connectors 156,156' are tightened for securing the vertical bars 158,158' of the posterior lingual section 152 to the lower anterior lingual arch wire 154, which in turn, is bonded to the lingual crown surface of the lower anterior teeth; and the crimpable tubes 174,174' are firmly crimped for securing the strip bases 172,172' to the lateral arms 160,160'.

Sagittal and vertical adjustments over treatment time are similar as for the fixed labial FOMA II 16 (FIG. 1).

Referring now to FIGS. 15, 16 and 17, a removable lingual FOMA II indicated generally by the reference numeral 178 will be described, which is also suitable for orthodontic expansion of a constricted dental arch concurrent with the skeletal correction. The lingual appliance 178 includes an upper part 179 having an upper plate 180, and a lower part 181 having a lower plate 182. The upper and lower plates 180,182 are positioned in the lingual side of the dental arches and secured to the dental arches by various removable attaching or anchorage means. The removable anchorage means (e.g. clasps) provide anchorage by contacting the dental arch at undercut areas.

Spring clasps 183 known as Adams clasps, attach the plates 180,182 to the molars U6,U6',L6,L6'. Each clasp 183 is anchored to the plates 180,182 by mesial and distal anchor arms 184,185. The clasp 183 extends around the corresponding molar from mesial anchor arm 184 to the distal anchor arm 185, and resiliently contacts the molar at the mesial and distal buccal embrasures 188,189. Clasps 190 having triangular ends 191 extend in the buccal embrasure between two adjacent teeth and is anchored in the plates 180,182 by an anchor arm 192.

Upper labial bow 193 (FIGS. 15,17) and lower labial bow 194 (FIG. 16) extend around the labial side of the anterior teeth and are secured to the plates via anchor arms 195,195'. "U" shaped loops 196,196' are positioned forward of the upper deciduous canines U3d, U3d'. As may be seen in FIG. 16, lower "U" shaped loops 197,197' have extended arms 198,198' to snap into cleat brackets 199,199' of the lower permanent canines L3,L3'. Cleat brackets 199, 199' bonded on the labial crown surface of the anterior teeth afford further anchorage for the upper labial bow 193 or the lower labial bow 194.

An upper magnetic arrangement 200 is attached to a substantially "U" shaped frame 201 and positioned anteriorly in the lingual side of the upper dental arch. The frame 201 (FIG. 17) comprise first right angled bar 202 having a sagittal portion 204 and a transverse portion 206, and a second right angled bar 208, having a sagittal portion 210 and a transverse portion 212. The transverse portion 206 telescopes within the transverse portion 212.

Retention arms 214,214' extending laterally from the transverse portions 206,212 of bars 202,208 respectively are secured to the upper plate 180. The posterior ends 218,218' of bars 202,208 are attached (soldered) to an expansion jack screw identified generally by the reference numeral 220.

The upper magnetic arrangement 200 includes two separate left and right magnetic units 222,222' seated in support bases 223,223' respectively. Tubular members 224,224' are attached to the supporting bases 223,223' respectively and receive respectively the sagittal portions 204,210 of bars 202,208. Each tubular member 224 and 224' includes a screw arrangement 232,232' for adjusting the antero-posterior position of the corresponding magnetic units 222,222'.

The expansion jack screw 220 comprises left and right screw housings 234,234', a double ended threaded shaft 236 threaded to both housings 234, 234', and anterior guiding rod 237 and posterior guiding rod (not shown) also inserted in both housings 234,234'. The double ended threaded shaft 236 has a centered head 238 having key opening 239.

Upon inserting a key (not shown) into the key opening 239 and rotating the double ended threaded shaft 236 in one direction, the shaft 236 will move medially (outward) from both screw housings 234, 234', thereby thrusting the left and right sections of the plate 180, against the corresponding upper dental quadrant imposing a transversal expansion of the upper dental arch. The guiding rods 237 lying parallel to each other and to the threaded shaft provide additional support for a parallel opening of the expansion jack screw 220.

Revolving the double ended threaded shaft 236 in counter direction will decrease the gap betweeen the screw housings 234,234' causing a release of the expansion force against the left and right sections of the upper dental arch, or in the case of further turns to produce a constriction of the upper dental arch and prevent expansion thereof.

As the screw housings 234, 234' move outwardly or inwardly as the case may be, the magnetic units 222,222' and the transversal portions 206,212 similarly move outwardly or inwardly.

A transverse bar 240 (FIG. 15) is positioned anteriorly on the lingual side of the lower dental arch and is attached at the opposite or left and right ends 241,241' to the lower plate 182 of the lower part 181 of the removable lingual Functional Orthopedic Magnetic Appliance 178. Centrally postioned on the bar 240 is a dove tail support table 244 having a dove tail tongue 245, which is similarly constructed as the table 164 in FIG. 13, for the receiving the lower anterior magnetic member 246 (shown in phantom).

The lower anterior magnet 246 has a greater transversal dimension than the combined transversal dimensions of the upper magnetic members 222,222' and any spacing therebetween, to compensate for any expansion gain in the transversal dimension due to treatment for expanding of the upper dental arch member.

The sagittal adjustments of the upper anterior magnetic arrangement 200 with respect to the lower anterior magnetic member 246, the vertical adjustment of the lower magnet 246 and the interaction between the magnets are similar as was described for the fixed lingual FOMA II 110 in FIG. 13. Thus, to vary the sagittal antero-posterior distance, the screws 232,232' are loosened and the tubular members 224,224' with the corresponding supporting bases 223,223' and the upper magnetic members 222,222' are moved forward or backward respectively along the sagittal portions 204,210. For adjustment of the vertical distance between the upper magnetic members 222,222' and the lower anterior magnetic member 246, an intermediate connector(s) similar to the connector 52 shown in FIG. 4 may be used, but having a dovetail groove interfacing the support table 244 and a centrally positioned dove tail tongue interfacing the lower anterior magnetic member 246. Correspondingly, the lower anterior magnetic member 246 has a centrally positioned dove tail groove on its inferior side.

Turning now to FIG. 18, the upper part 250 of a removable lingual FOMA III 252 will be described for the correction of a skeletal Class III malocclusion (lower jaw protrudes further anteriorly than the upper jaw). The upper part 250 includes an upper plate 254 affixed and supported on the upper dental arch using the several spring clasps 183,190, upper labial bow 193 and cleat brackets 199,199' such as are used for attaching the removable lingual FOMA II 178 to the dental arches of the upper and lower jaws 12,14 (FIG. 15). An anterior arcuate magnetic unit 256 is adjustably supported on a screw driven framework 258.

The screw driven framework 258 comprises a retraction screw arrangement 260 and a quadrilateral guiding unit 262 both linked together. The retraction screw 260 supporting the magnetic unit 256 controls the anterio-posterior adjustments of the anterior arcuate magnetic unit 256 with the guiding unit 262 adding stabilization to the assemblage.

The retraction screw arrangement 260 includes a threaded shaft 264, a nut housing 266, a substantially "U" shaped bar 268 having a transversal portion 270 affixed to the magnetic unit 256 and two sagittal arms 272,272'. The head 275 of the threaded shaft 264 is linked in a pivot joint to a transversal connector 276. The connector 276 is permanently affixed to the sagittal arms 272,272' of the "U" shaped bar 268.

The quadrilateral guiding unit 262 comprises a forward transversal bar 277 anchored to the upper plate 254 and a backward transversal bar 278 and each joined to a pair of sagittal bars 280,280'. The backward bar 278 is also attached by solder or otherwise to the nut housing 266 of the retraction screw 260. A pair of sagittal sleeves 284,284' are attached to the magnetic unit 256 and respectively receive the sagittal bars 280,280'.

Upon activation of the screw shaft 264 for rotating in the nut housing 266, the "U" shaped bar 268 of the retraction screw arrangement 260 moves in the antero-posterior direction, thereby dragging its two sagittal arms 272,272' in the same direction. During such antero-posterior movements the qradrilateral guiding unit 262 provides support for the assemblage via the sleeves 284,284' of the magnetic unit 256 which slide or move along the sagittal bars 280,280' of the quadrilateral unit 268.

The lower part (not shown) of the lingual FOMA III 252 may be similar to the lower part 181 of the lingual FOMA II 178 shown in FIG. 15, except that the occlusal surfaces of the upper and lower magnetic unit 286, 322 (FIG. 20b) incline downward from the anterior side 287 to the posterior side 288.

Turning now to FIG. 19, an extra oral appliance such as a headgear indicated generally by the reference numeral 290 is used for pulling the upper jaw 12 in the posterior direction in the treatment of skeletal Class II malocclusions, and may be integrated with the upper part 291 of a fixed labial FOMA II 16 as shown in FIG. 1 or with a removable lingual FOMA II 178 (FIG. 15).

The magnetic headgear 290 includes an outer bow 292 having side portions 294,294' which extend outward from a central point 296. The ends 298,298' of the outer bow 292 are bent into hooks for supporting opposite ends of an elastic head band 300.

The extra-oral FOMA II 291 comprises a vertically adjustable anterior upper magnetic means 302 centrally attached to an inner magnetic bow 303 at the central point 296.

The upper anterior magnetic means 302 includes a cylindrically shaped and externally threaded housing 304, which is threaded into a corresponding threaded hollow 305 of the inner magnetic bow 303 at the central point 296. A slot 306 is formed in the superior (gingival) surface 308 of the magnetic means 302 to receive a screw driver for adjusting the vertical level of the magnetic means 302. Thus, the magnetic attractive force may be varied so there is no air gap between the upper magnetic means 302 and the lower anterior magnet 68,168 or 246 during mouth closure.

The inner bow 303 includes side arms 310,310' secured to the upper posterior teeth, in a manner similar to the attachment of the upper magnetic bow 18 to the upper jaw 12 (FIG. 1). Thus, the simultaneous action of the magnetic head gear 290 with a FOMA II appliance functions to correct a sagittal mandibular deficiency with a sagittal maxillary excess. Hence, the magnetic head gear 290 is forcing the upper jaw 12 in the posterior direction as the FOMA II appliance is causing the repositioning of the lower jaw 14 in the anterior direction.

In FIG. 20a, a skeletal class III malocclusion is shown, whereby the lower jaw 14 is overdeveloped and the upper jaw 12 has a sagittal deficiency. In FIG. 20b a schematic of a lingual FOMA III appliance 252 comprises an upper and lower parts 250, 320 is shown and includes a lower anterior magnetic arrangement 322 positioned sagittally anterior from the upper anterior magnetic arrangement 256. A retraction screw 260 is attached to the upper magnetic arrangement 256 for adjusting the sagittal position of the upper magnetic arrangement 256. During treatment, the upper magnetic arrangement 256 is incrementally displaced in the posterior direction for slightly increasing in successive intervals the sagittal distance between the upper and lower magnetic arrangements 256,322, for pulling and retracting the lower jaw 14 toward the upper jaw 12.

With the exception of the lower anterior magnet 326 of the lower magnetic arangement 322, the lower part of the removable lingual FOMA III 320 is identical to the lower part of the removable lingual FOMA II 181 (FIG. 15) comprising the lower plate 182, the transverse bar 240, the centrally positioned dove tail support table 244 and anchorage means including adams clasps 183, 183', triangle clasps 190,190', lower labial bow 194 and cleat brackets 199,199' supporting the lower labial bow 194. Likewise, vertical adjustment of the lower magnetic arrangement 322 is performed by means of intermediate connectors(s) as used for the removable FOMA II 181. As shown in FIG. 20b, the upper and lower occlusal surfaces 332, 334 of the anterior magnetic arrangements 256,322 incline downward from the anterior ends 335, 336 to their postior ends 337, 338.

Various modifications of the invention of functional orthopedic magnetic appliances described herein, are within the spirit and scope of the invention, the scope of which is limited solely and defined by the appended claims.

I claim:

1. A functional orthopedic magnetic appliance ("FOMA") for correcting skeletal malocclusions (Class II & Class III) of the upper and lower jaws over treatment time when one of the jaws protrudes further anteriorly within a sagittal plane than the other jaw, comprising:

an upper support secured to the teeth of the upper jaw;

an upper anterior magnetic unit mounted to the upper support adjacent to the anterior end of the upper dental arch;

a lower support secured to the teeth of the lower jaw;

a lower anterior magnetic unit mounted to the lower support adjacent to the anterior end of the lower dental arch, said anterior magnetic unit associated with said protruding jaw being positioned anterior from said other magnetic unit when the mouth is in an open condition and substantially no magnetic force is present, the poles of said upper and lower magnetic units being arranged for magnetically attracting each other, said lower magnetic unit contacting said upper magnetic unit to pull the lower jaw toward the upper jaw in the direction to reduce the malocclusion when the mouth moves toward a closed condition; and sagittal adjustment means associated with one of the anterior magnetic units for varying the distance of said one anterior magnetic unit from the corresponding anterior end of the dental arch in the postero-anterior direction within the sagittal plane and simultaneously increasing the sagittal distance between the upper and lower anterior magnetic units to increase the force acting on said lower jaw but maintaining the anterior magnetic unit associated with the protruding jaw anterior from the other anterior magnetic unit, when the mouth is in said open condition during said treatment time.

2. The magnetic appliance of claim 1, wherein said upper jaw jetting further anteriorly than the lower jaw (skeletal Class II malocclusion) within said sagittal plane, said upper anterior magnetic unit being positioned sagittally anterior from said lower anterior magnetic unit when the mouth is in said open condition, said sagittal adjustment means being associated with at least one of the magnetic units for periodic adjustment during said treatment time to provide partial correction of the skeletal Class II malocclusion for each adjustment by increasing the sagittal distance between said anterior magnetic units when the mouth is in said open condition, to increase the protrusive force acting on the lower jaw and maintaining the contact between said anterior magnetic units when the mouth moves toward a closed condition.

3. The magnetic appliance of claim 1, wherein said lower jaw jetting further anteriorly than the upper jaw (skeletal Class III malocclusion) within said sagittal plane, said lower anterior magnetic unit being positioned anterior from said upper anterior magnetic unit when the mouth is in said open condition, said sagittal adjustment means being adjusted periodically to provide partial correction of the skeletal malocclusion by increasing the sagittal distance between said magnetic units when the mouth is in said open condition, to increase the retractive force acting on the lower jaw and maintaining the upper and lower anterior magnetic units in contact when the mouth moves toward the closed condition.

4. The magnetic appliance of claim 2, wherein:
said upper anterior magnetic unit is located labially from the anterior end (incisal edge) of the upper dental arch; and
said lower anterior magnetic unit is spaced labially or lingually from the anterior end (incisal edge) of the lower dental arch.

5. The magnetic appliance of claim 2, wherein:
said upper anterior magnetic unit is located lingually from the anterior end (incisal edge) of the upper dental arch; and
said lower anterior magnetic unit is located labially or lingually from the anterior end (incisal edge) of the lower dental arch.

6. The magnetic appliance of claim 3, wherein:
said upper anterior magnetic unit is located labially from the incisal edge of the upper dental arch; and
said lower anterior magnetic unit is located labially or lingually from the incisal edge of the lower dental arch.

7. The magnetic appliance of claim 3, wherein:
said upper anterior magnetic unit is located lingually from the anterior end of the upper dental arch; and
said lower anterior magnetic unit is located labially or lingually from the anterior end of the lower dental arch.

8. The magnetic appliance of claim 1, wherein a sagittal cross section of either said upper and lower anterior magnetic units is substantially a right angle trapezoid with the respective oblique sides forming the planes interfacing between the upper and lower anterior magnetic units.

9. The magnetic appliance of claim 2, wherein the contacting interface between said upper and lower anterior magnetic units slopes upward (superiorly) from the anterior toward the posterior direction.

10. The magnetic appliance of claim 3, wherein the contacting interface between said upper and lower anterior magnetic units slopes downward (inferiorly) from the anterior toward the posterior direction.

11. The magnetic appliance of claim 1 includes:
a vertical adjustment means associated with either of the magnetic units for varying the vertical distance between the upper anterior magnetic unit and the lower anterior magnetic unit.

12. The magnetic appliance of claim 1 includes:
at least one upper posterior magnet attached to a posterior tooth of the upper dental arch and positioned posterior from the upper anterior magnetic unit; and
at least one lower posterior magnet attached to a posterior tooth of the lower dental arch and positioned posterior from the lower anterior magnetic unit, said posterior magnet associated with the anterior protruding jaw being positioned sagittally anterior from the other posterior magnet when the mouth is in said open condition, said upper posterior magnet overlapping said lower posterior magnet when the upper and lower magnetic units are in contact as the mouth moves to a closed condition, to cause vertical movement of the posterior teeth simultaneously with the repositioning of the lower jaw during said treatment time.

13. The appliance of claim 12, wherein said upper posterior magnet and said lower posterior magnet are in a magnetically repulsive configuration to cause intrusion of posterior dental segments.

14. The appliance of claim 12, wherein said upper posterior magnet and said lower posterior magnet are in an attractive configuration, to cause extrusion of posterior dental segments.

15. The magnetic appliance of claim 12 includes anchoring means attached to the same dental arch associated with said sagittal adjustment means, one of said posterior magnets secured to said anchoring means and being sagittally movable therealong for varying the sagittal distance between said upper posterior magnet and said lower posterior magnet to correspond to the adjustment made during said treatment period in the sagittal distance between said upper and lower anterior magnetic units when the mouth is in said open condition, so that said upper posterior magnet and said lower posterior magnet overlapping when the mouth is in said closed condition.

16. The magnetic appliance of claim 1, wherein at least one of said supports includes a magnetic bow comprising:
- a left side portion extending along the left buccal side of the corresponding dental arch and a right side portion extending along the opposite right buccal side of the dental arch, each of said portions having an anterior end and a posterior end;
- one of the magnetic units secured between the anterior ends of the side portions of the magnetic bow, said one magnetic unit being positioned anterior from the incisal edge of the dental arch; and
- connecting means for securing the posterior ends of the side portions of the bow to adjacent posterior teeth of the dental arch.

17. The magnetic appliance of claim 16, wherein said connecting means includes:
- a band attached to one of said posterior teeth; and
- a tube secured to said band at the buccal side of said one posterior tooth, said posterior end of the magnetic bow removably secured inside said tube and insertible to various sagittal locations therein for varying the sagittal distance between said one anterior magnetic unit and the other anterior magnetic unit.

18. The magnetic appliance of claim 16 includes:
- an anchorage means for attaching a side portion of the magnetic bow to the buccal side of an adjacent tooth between the anterior and posterior ends of the corresponding side portion.

19. The magnetic appliance of claim 16 includes:
- a base secured to the surface of a tooth;
- a cleat attached to said base;
- a sleeve having a clasp thereon positioned on one of said side portions of the magnetic bow and secured adjacent said cleat; and
- a hook attached to sleeve and connecting said cleat and said sleeve for securing said one side portion to the corresponding jaw.

20. The magnetic appliance of claim 13, wherein the magnetic repulsive force between said upper and lower juxtaposed posterior magnets is less than the magnetic attractive force between said upper and lower anterior magnetic means, to enable the sagittal displacement of the lower jaw during said treatment time.

21. The magnetic appliance of claim 1, wherein said sagittal adjustment means includes:
- a support member for receiving one of said anterior magnetic units, said one anterior magnetic unit being positioned anterior from the support member; and
- an anterior intermediate connector member for inserting or removing from between said support member and said one anterior magnetic unit for varying the sagittal distance between said one magnetic unit and the corresponding dental arch, and thereby varying the sagittal distance between said one anterior magnetic unit and the other anterior magnetic unit in the other jaw, said support member and said one magnetic unit and said intermediate connector member being located within a sagittal plane.

22. The magnetic appliance of claim 12, wherein said vertical adjustment means comprises:
- a vertical supporting member for receiving one of said anterior magnetic units, said one anterior magnetic unit being at a different vertical level than said vertical supporting member; and
- an intermediate member for inserting between the vertical supporting member and said one anterior magnetic unit for changing the vertical distance between said one magnetic unit and the other anterior magnetic unit in the opposite jaw, said vertical supporting member and the associated magnetic unit being located within a vertical plane.

23. The magnetic appliance of claim 22, wherein one of said members includes grooves and the other of said members includes tongues for fitting into said grooves.

24. The magnetic appliance of claim 17 wherein: said tube having an open position and a locked position, said tube receiving said posterior end of the side portion when in the open position and said posterior end being secured in said tube when in the locked position.

25. The magnetic appliance of claim 1, wherein one of said anterior magnetic means includes:
- an internally threaded holder; and
- an externally threaded magnet received in said holder and movable therein for varying the vertical distance between said one anterior magnetic means and the other said anterior magnetic means to provide said vertical adjustment means.

26. The magnetic appliance of claim 1 further comprises an upper part comprising:
- an upper anterior arch wire secured to the lingual side of the upper anterior dental arch;
- a pair of sagittal bars spaced apart and parallel to each other, each said sagittal bars including an anterior end and a posterior end, said anterior ends being secured to the anterior arch wire;
- said upper anterior magnetic units movable along said sagittal bars for varying its sagittal position;
- securing units for securing the upper anterior magnetic means to the sagittal bars; and
- mounting means for securing the posterior end of the sagittal bars to the lingual side of the upper posterior dental arch.

27. The magnetic appliance of claim 26 further includes a support for supporting the upper anterior magnetic units and a pair of hollow tubes secured to the support, said sagittal bars extending through said tubes, said securing means securing the tubes to the sagittal bars at the desired location thereon.

28. The magnetic appliance of claim 27, wherein said securing means includes:
- a threaded hole formed in each said tube; and
- a screw threadedly received in said threaded hole for tightening against the sagittal bars.

29. The magnetic appliance of claim 27, wherein said mounting means includes:
- a substantially "U" shaped rod member having a pair of side rod portions and a transversal rod;
- a pair of spaced apart hollow tubes attached to the transversal rod portion, each of said posterior portions of the sagittal bars extending through one of said tubes;
- attaching means for securing the tubes of the transversal rod to the said posterior portions of the corresponding sagittal bars; and
- connecting means for attaching the side rod portions to said lingual tubes secured to bands attached to the posterior dental arch.

30. The magnetic appliance of claim 1, further includes a lower part comprising:
- a lower anterior arch wire secured to the lingual side of the lower anterior dental arch;

a pair of side arms each having an anterior end and a posterior end;

a transversal portion connected between the anterior ends of said side arms, said posterior ends of said arms being inserted into tubes secured to bands attached to the posterior arch, said anterior magnetic means being supported on said transversal portion; and connecting means for connecting said lower anterior arch wire to said vertical extension of the anterior portion of the side arms.

31. The magnetic appliance of claim 30 wherein said transversal portion includes:

a support table having a left wing and a right wing, said lower anterior magnetic unit secured to said support table; and a left holder and a right holder for movably receiving said left wing and said right wing respectively.

32. The magnetic appliance of claim 12 includes means for varying the vertical position of at least one of said posterior magnet to correspond to vertical adjustment of said anterior magnetic means so that upper and lower posterior magnets and upper and lower anterior magnetic means will operate each with no air-gap.

33. The magnetic appliance of claim 31, wherein:

said left holder includes an anterior left track and a posterior left track for receiving said left wing and said right holder includes an anterior right track and a posterior right track for receiving said right wing.

34. The magnetic appliance of claim 1, wherein said upper anterior magnetic unit is positioned on the lingual side of the upper dental arch and includes a right magnetic part and a left magnetic part; and means for moving said right magnetic part toward or away from the left magnetic part.

35. The magnetic appliance of claim 34, includes a plate abutting against the lingual side of the lower dental arch, said plate applying an outward force against said lingual side of the lower dental arch for expanding the transversal dimensions of the lower dental arch, and simultaneously the right and left parts of the anterior magnetic means move away from each other.

36. The magnetic appliance of claim 34 further includes:

a right support base and a left support base for holding said right and left magnetic parts respectively, and said sagittal adjustment means includes:

a tube member secured to each of said support bases;

a left right angle bar and a right right angle bar spaced sagitally apart and passed one within each other in the transversal direction, each right angle bar is attached anteriorly to the plate and posteriorly to the expansion means, each of said support bases movable along the corresponding said bar for adjusting the antero-posterior position of the corresponding magnetic part; and attaching means for securing the magnetic part at the desired sagittal position on the corresponding bar.

37. The magnetic appliance of claim 1 includes:

a plate positioned on the lingual side of one of said jaws;

one of said anterior magnetic means attached to said plate;

a labial bow extends around the labial side of the anterior teeth of said one jaw;

anchorage means for securing the labial bow to said anterior teeth; and anchor arms extend from opposite ends of the labial bow to said plate to secure the labial bow to the plate.

38. The magnetic appliance of claim 37, wherein:

said anchorage means includes a cleat bracket attached to the labial surface of an anterior tooth, said labial bow being a single wire; and one end of said labial bow being looped adjacent said cleat bracket, said loop includes an extension anchor arm in the form of double strained wire to be hooked into the cleat bracket.

39. The magnetic appliance of claim 37, wherein said means for moving said right and left magnetic parts includes:

a screw adjustment means causing said right magnetic part to move away from the left magnetic part when rotated in one direction and to cause said right magnetic part to move toward said left magnetic part when rotated in the opposite direction;

a tubular member associated with one of the magnetic parts; and a rod member extending inside the tubular member and associated with the other magnetic part, said rod member moving inward inside the tubular member when the right and left magnetic parts move toward each other and moving outward inside the tubular member when the magnetic parts move away from each other.

40. The magnetic appliance of claim 1, wherein said sagittal adjustment means includes:

a support member associated with one of said anterior magnetic unit;

a screw arrangement attached to said support member for moving said one anterior magnetic unit sagittally in the posterior direction when the screw arrangement is rotated in one direction and moving said one magnetic unit sagittally in the anterior direction when the screw arrangement is rotated in the opposite direction;

a pair of spaced apart tubes secured to said one anterior magnetic unit; and a first bar extending through one of said tubes and a second bar extending through the other tube and said bars are fixedly attached to the plate, said tubes associated with the anterior magnetic unit moving along said bars responsive to the sagittal adjustment of the screw arrangement.

41. The magnetic appliance of claim 2 includes:

posterior force means urging said upper jaw sagittally in the posterior direction simultaneously as said lower jaw moves sagittally in the anterior direction toward the upper jaw in response to the attractive force of said anterior magnetic means.

42. The magnetic appliance of claim 41, wherein said posterior for means is an upper magnetic headgear comprising: an inner bow secured to the upper jaw, an outer bow having side portions extending from inside the mouth to the outer border of the cheek;

a tension means attached to said side portions and extending across the back of the head for securing the head gear to the head; and an anterior magnetic means secured to the anterior portion of the headgear.

43. A functional orthopedic magnetic appliance ("FOMA") for correcting skeletal malocclusions (Class II & Class III) of the upper and lower jaws over treatment time when one of the jaws protrudes jets sagittally further outward anteriorly within a sagittal plane than the other jaw, comprising:
- an upper support secured to the teeth of the upper jaw;
- an upper anterior magnetic unit mounted to the upper support and spaced from the anterior end of the upper dental arch;
- a lower support secured to the teeth of the lower jaw;
- a lower anterior magnetic unit mounted to the lower support and spaced from the anterior end of the lower dental arch, said anterior magnetic unit associated with said protruding jaw being positioned anterior from said other magnetic unit when the mouth is in an open condition and substantially no magnetic force is present, the poles of said upper and lower magnetic units being arranged for magnetically attracting each other, said lower magnetic unit contacting said upper magnetic unit to pull the lower jaw toward the upper jaw in the direction to reduce the malocclusion when the mouth moves toward a closed condition; and
- sagittal and or vertical adjustment means associated with at least one of the anterior magnetic units for varying the distance of said one anterior magnetic unit from the corresponding anterior end of the dental arch in the postero-anterior direction and/or gingivo-occlusal direction respectively within the sagittal plane and simultaneously varying the sagittal and/or vertical distance between the upper and lower anterior magnetic units but maintaining the anterior magnetic unit associated with the protruding jaw anterior from the other anterior magnetic unit in the opposite jaw when the mouth is in said open condition during said treatment time, and also maintaining contact between the upper and lower magnetic units when the mouth is in the closed condition.

44. In a method for correcting Class II or Class III malocclusions including the steps of:
- securing an upper magnetic unit to the upper dental arch adjacent the incisal edge thereof;
- securing a lower magnetic unit to the lower dental arch adjacent the incisal edge thereof;
- orientating the magnetic units in a magnetically attractive arrangement;
- spacing the magnetic units initially at a substantially predetermined sagittal distance apart when the mouth is open and substantially no magnetic force is present between the units;
- contacting the magnetic units when the mouth moves to a closed condition; and
- increasing the sagittal distance between the magnetic units when the mouth is open after the distance between the magnetic units has decreased from said predetermined distance due to a partial correction of the skeletal malocclusion.

* * * * *